(12) United States Patent
Chan et al.

(10) Patent No.: US 10,918,290 B2
(45) Date of Patent: Feb. 16, 2021

(54) MULTI-CHANNEL VITALS DEVICE

(71) Applicant: The DNA Medicine Institute, Inc., Cambridge, MA (US)

(72) Inventors: Eugene Y. Chan, Boston, MA (US); Dexter Eames, Cambridge, MA (US); Marcus Atkin, Derby (GB)

(73) Assignee: DNA Medicine Institute, Inc., Cambridge, MA (US)

( * ) Notice: Subject to any disclaimer, the term of this patent is extended or adjusted under 35 U.S.C. 154(b) by 102 days.

(21) Appl. No.: 16/194,744

(22) Filed: Nov. 19, 2018

(65) Prior Publication Data
US 2019/0150762 A1    May 23, 2019

Related U.S. Application Data

(63) Continuation of application No. 15/143,560, filed on Apr. 30, 2016, now Pat. No. 10,251,565.

(60) Provisional application No. 62/154,758, filed on Apr. 30, 2015, provisional application No. 62/154,788, filed on Apr. 30, 2015, provisional application No. 62/154,967, filed on Apr. 30, 2015.

(51) Int. Cl.
| | | |
|---|---|---|
| *A61B 5/0205* | (2006.01) | |
| *A61B 5/1455* | (2006.01) | |
| *A61B 5/0402* | (2006.01) | |
| *A61B 5/00* | (2006.01) | |
| *A61B 5/08* | (2006.01) | |
| *A61B 5/024* | (2006.01) | |

(52) U.S. Cl.
CPC .......... *A61B 5/02055* (2013.01); *A61B 5/002* (2013.01); *A61B 5/0402* (2013.01); *A61B 5/0816* (2013.01); *A61B 5/14551* (2013.01); *A61B 5/6833* (2013.01); *A61B 5/02438* (2013.01); *A61B 2562/0238* (2013.01); *A61B 2562/0271* (2013.01); *A61B 2562/06* (2013.01)

(58) Field of Classification Search
None
See application file for complete search history.

(56) References Cited

U.S. PATENT DOCUMENTS

| | | |
|---|---|---|
| 7,020,508 B2 | 3/2006 | Stivoric et al. |
| 7,257,438 B2 | 8/2007 | Kinast |
| 7,431,696 B1 | 10/2008 | Brady et al. |
| 7,539,532 B2 | 5/2009 | Tran |
| 8,214,007 B2 | 7/2012 | Baker et al. |
| 9,282,924 B2 | 3/2016 | Lin et al. |
| 2013/0237772 A1 | 9/2013 | Pisani et al. |
| 2014/0236037 A1 | 8/2014 | Banet et al. |
| 2015/0094552 A1 | 4/2015 | Golda et al. |
| 2015/0248833 A1 | 9/2015 | Ame et al. |
| 2015/0272452 A1 | 10/2015 | Mullin et al. |

(Continued)

FOREIGN PATENT DOCUMENTS

WO  WO2015/0162566  10/2015

*Primary Examiner* — Brian T Gedeon
(74) *Attorney, Agent, or Firm* — Danielson Legal LLC

(57) ABSTRACT

An integrated vitals device capable of acquiring multiple data streams, allowing for comprehensive measurement of whole health status using a single, compact device. This allows for simplification of traditional healthcare delivery where multiple devices are required for acquisition of vital signs. A sensor stack up, occupying the approximate physical footprint and volume allows this approach to be possible. This application describes how these simultaneous vitals data streams can be acquired using an integrated device with small mass and volume.

18 Claims, 9 Drawing Sheets

(56) References Cited

U.S. PATENT DOCUMENTS

2015/0327775 A1    11/2015   Carter
2016/0022213 A1     1/2016   Lee
2016/0302674 A1    10/2016   Moyer
2018/0028122 A1     2/2018   Golda et al.

MULTI-CHANNEL VITALS DEVICE

CROSS-REFERENCE TO RELATED APPLICATIONS

The present application is a continuation of U.S. patent application Ser. No. 15/143,560, filed on Apr. 30, 2016, which claims the benefit of and priority to each of U.S. Provisional Appl. No. 62/154,758, filed on Apr. 30, 3015, U.S. Provisional Appl. No. 62/154,788, also filed on Apr. 30, 2015, and U.S. Provisional Appl. No. 62/154,967, also filed on Apr. 30, 2015. The entire disclosure of each of these applications is incorporated by reference as if set forth in their entirety herein.

STATEMENT REGARDING FEDERALLY SPONSORED RESEARCH OR DEVELOPMENT

This work was funded in part via NASA Contract NNX14CJ25P.

TECHNICAL FIELD

The field relates to the development of a novel integrated vitals sensor for comprehensive and wireless measurement of electrocardiogram (EKG), oxygen saturation (SpO2), heart rate, respiratory rate, blood pressure, and core body temperature. The sensor utilizes unique packaging and integration to achieve measurement of important vital signs using a single, small package sensor.

BACKGROUND

The wireless monitoring of vital signs is particularly important for remote health monitoring. This allows patients and consumers to monitor their health with greater flexibility than traditional wired approaches. Recently, with the advent of Bluetooth technology, and in particular, Bluetooth Low Energy (BLE), remote sensing has gained more capabilities. This allows devices to be paired with apps on smartphones. These basic technologies have inspired the new wave of wearables for health and fitness. There does not exist, however, a comprehensive technology that measures important medical vital signs in a continuous manner. Most approaches fail to measure one or more of the important vital signs.

EKG is conventionally measured by the use of 12-lead systems in the hospital. For portability, the Holter monitor is utilized to capture cardiac events over the course of an extended time period. Unfortunately, this approach is difficult because it requires the attachment of wires to various parts of the body and then a sizable battery-powered unit that is worn on the belt. After a certain time period of recording, data is transmitted over the telephone. This method is still in use today and is a means to capture cardiac events from patients. The size and weight of the unit makes it cumbersome for most users.

Measurement of pulse oximetry is done using a finger probe. The probes shine a red light and an infrared light through the finger and then measures the change in absorbance from beat-to-beat. The relative ratio of the absorbance is presented as the ratio of ratios, the ratio of the AC signal of red over the DC signal of red over the AC signal of infrared over the DC signal of infrared. This ratio method corrects for any DC drift in the system and allows the ratios of the two wavelengths to be measured accurately. At 660 nm, deoxygenated hemoglobin Hb absorbs more than oxygenated hemoglobin HbO2. At 910 nm infrared, the HbO2 absorbs more than the Hb. The finger probes can be worn briefly, but interfere with daily life and tasks.

It is easy to measure skin temperature in a continuous manner or to measure core temperature in a single measurement. However, continuous core body temperature measurement is challenging. This would require an internal probe in the gastrointestinal tract, a catheter, or some other internal probe. These are invasive and cannot be utilized in routine settings for consumers and patients. Core body temperature fluctuations can happen quickly, signaling worsening infection or some other process that needs medical attention fast.

Heart rate and respiratory rate are important physiological parameters that give significant insight into health and wellness. Heart rate is readily derived from both photoplethysmograph (PPG) and EKG signals. Weak EKG or PPG signals can lead to inaccuracies and ideally, the heart rate and respiratory rates can be redundantly analyzed from both data traces.

Blood pressure measurements are currently performed utilizing cuff-based approaches, typically a sphygmomanometer that is applied around the arm. Inflation of the cuff using a rubber bulb occludes blood flow allowing for determination of blood pressure. Both the systolic and diastolic blood pressures can be determined by listening to the Korotkoff sounds generated during this process. The sounds are heard using a stethoscope and interpreted by a skilled medical professional. This approach gives only, individual and not continuous blood pressure readings.

There are significant challenges that need to be overcome in order to have continuous measurement of core vital signs, especially in a small, low power form factor.

SUMMARY

The subject of this invention is focused on the measurement of multiple data streams in a unique optical, electrical, and mechanical device for continuous measurement of core vital signs. The approach taken leverages unique approaches to acquiring multiple data streams with a single small form factor device. This is possible through the use of a simultaneous function electromechanical stack up. This simultaneous stack up allows for multiple functions in the same physical space, allowing achievement of a small form factor device, capable of acquiring multiple data streams simultaneously.

The stack up includes integration of a reflective pulse oximeter, one-lead EKG, resistive heater, a vertical set of thermistors that measure heat radiating from the body, thermistor lens, and a double-sided adhesive gel pad. At the minimum, the stack up has a printed circuit board (PCB) that has a one-lead EKG with a reflective pulse oximeter. This allows for simultaneous measurement of at least two data streams. The heater and thermistor stack up allow for measurement of heat radiating from the body and a measurement of core body temperature to be determined. This adds the third data stream from which six core vital signs can be determined: heart rate, respiratory rate, EKG, SpO2, and core body temperature.

The PCB has an EKG chip, reflective pulse oximeter, resistive heater, and thermistors. The layout is arranged so that the resistive heater overlays the pulse oximeter. This allows for heating the stackup comprising the following: pulse oximeter, thermistors, and thermistor lens. The use of resistive heating elements onboard the PCB decreases the thickness of the unit. Normally, in electrical assemblies, any heating elements would be a separate layer or component from the main PCB. The PCB allows measurement of all these parameters on a single board.

Core body temperature is measured by heat radiating from the body. In addition, the use of a resistive heater on the PCB counteracts the heat radiating from the body, allowing the thermal resistance of the body to be determined, and thus the core body temperature to be measured. The use of more than one thermistor allows the determination of heat radiating from the body. This arrangement allows for accurate measurement of the core body measurement.

The stack up includes a thermistor lens, or a precision thermistor embedded in an optical element. The optical element is in contact with the body skin surface, allowing for good light transmission and simultaneous thermal contact of the body with the thermistor. The thermistor lens is custom molded to allow the lens or optical element to achieve two different functions at the same time. In the stack up, this allows the pulse oximeter to be directly overlayed on top of the core body temperature thermometer in the same physical and electromechanical space.

The adhesive gel pad is double-sided and allows for attachment of the vitals device to the skin. There is a skin side adhesive and a device side adhesive. This is clearly identified, by having two different colors for the sides. The surface area of the gel pad contact to the electrodes is sufficient to allow measurement of the body's electrical signals. There is an aperture in the gel pad that allows direct contact of the thermistor lens to the skin, allowing for optical and thermal coupling of any signals from the body. The stack up therefore includes the gel pad, which provides key features for interfacing the skin with the device.

The mechanical packages positions the EKG electrodes and the pulse oximeter aperture and thermistor lens on one side of the unit, allowing for simultaneous collection of multiple data streams from the individuals. Furthermore, the unit provides thermal insulation maximizing the temperature difference in the thermistors and allowing any unit heating to be retained largely within the device. The insulation decreases the power consumption of the unit, allowing continuous vitals on a single charge for a longer period of time.

By employing a simultaneous stack up of the electromechanical and optomechcanical package, multiple functions are achieved in the same physical space, allowing the overall vitals unit to be small, compact, and capable of measuring multiple vitals streams simultaneously.

DETAILED DESCRIPTION

Figure 1:
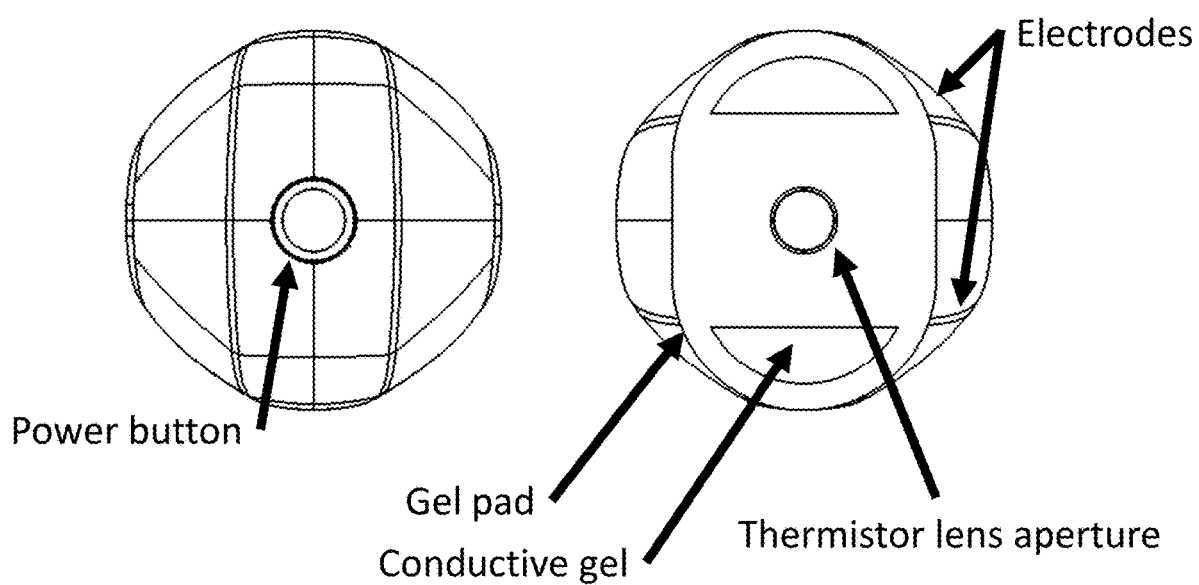
FIG. 1 shows the top and bottom view of the vitals device. The top view has the power button and the bottom of the device is attached to a removable gel pad that has conductive gel and an aperture for the thermistor lens.
Figure 2:
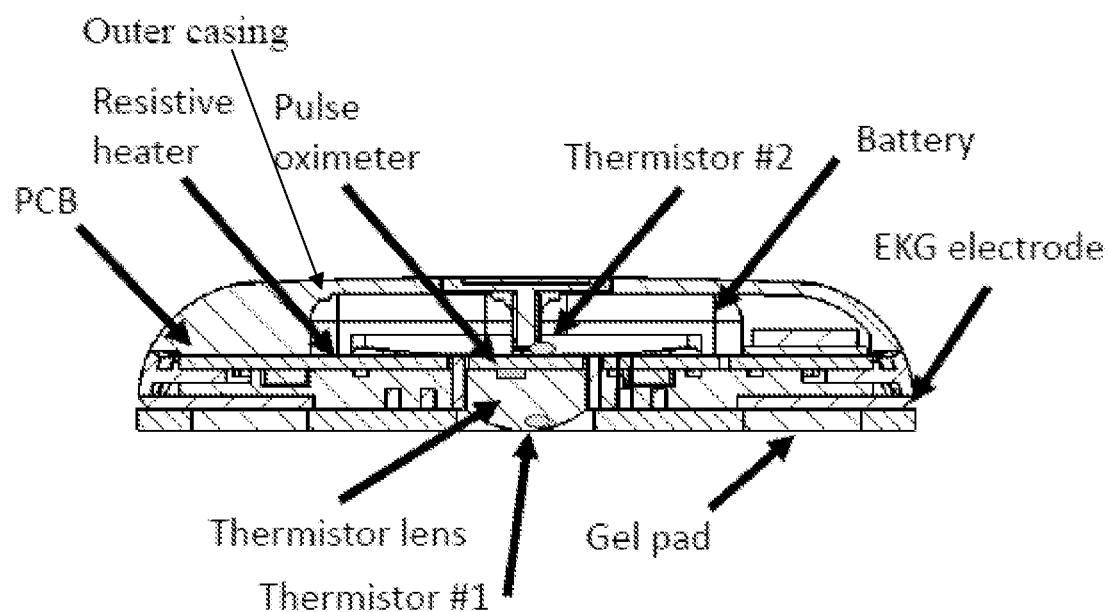
FIG. 2 shows the section view and stack up of the vitals device. This aperture in the gel pad allows for contact of the thermistor lens with the skin. Multiple thermistors allow for measurement of heat radiating from the body. The PCB is integrated to allow measurement of multiple vitals streams.
Figure 3:
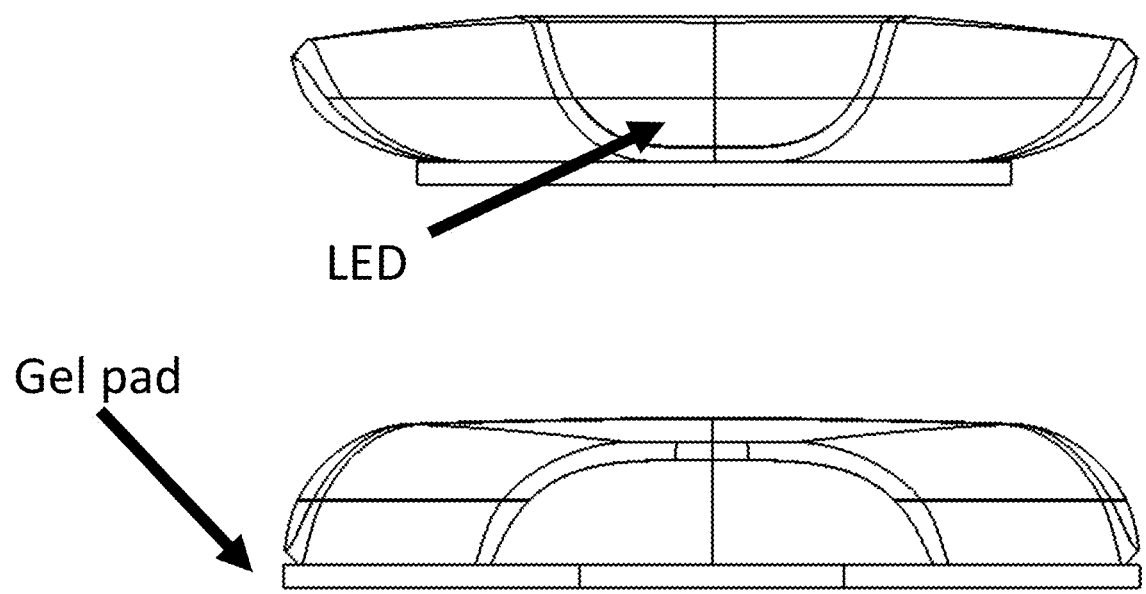
FIG. 3 shows the side views of the device. Two of the four sides have LEDs for indicating the status of the unit. The gel pad is evident from the side view.
Figure 4:
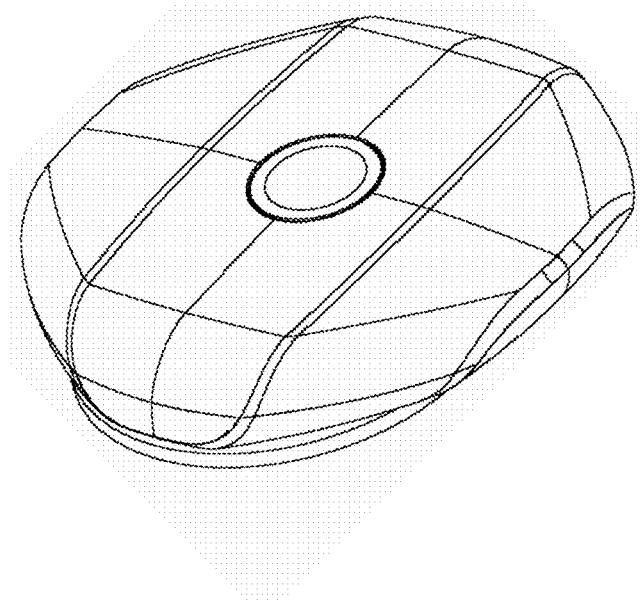
FIG. 4 shows the three-dimensional view of the device with the power button and the LED light.
Figure 5:
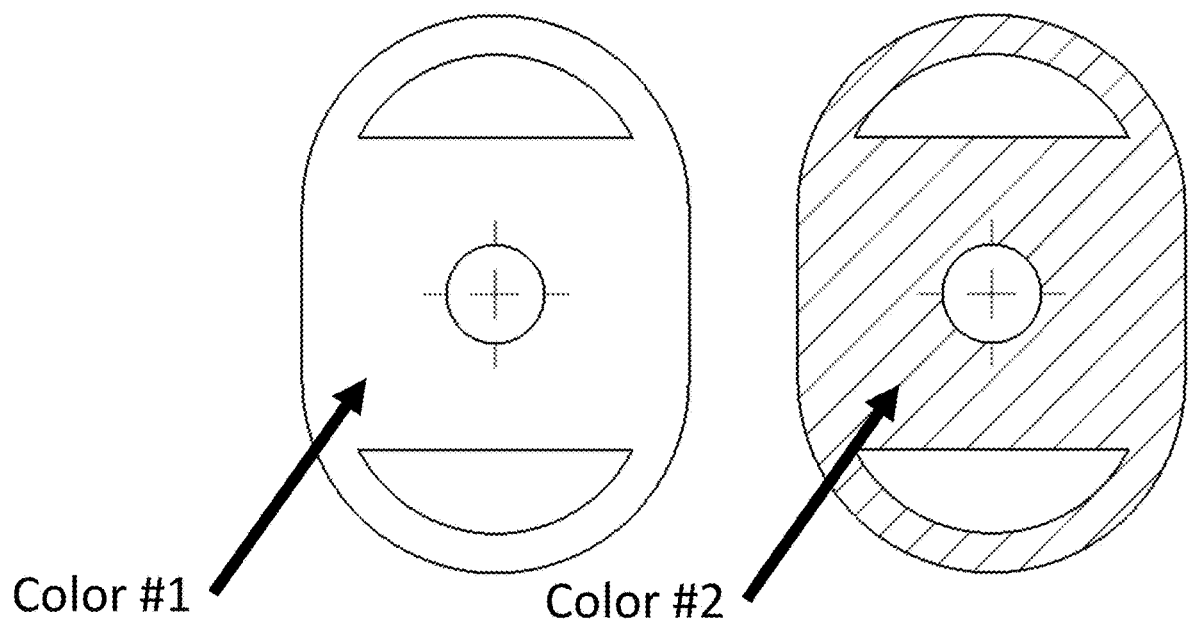
FIG. 5 shows the front and back of the gel pad. The semi-circular regions contain conductive gel. The aperture in the center allows for the thermistor lens to touch the skin. Both sides of the gel pad are different colors to allow for clear orientation of the gel pad.
Figure 6:
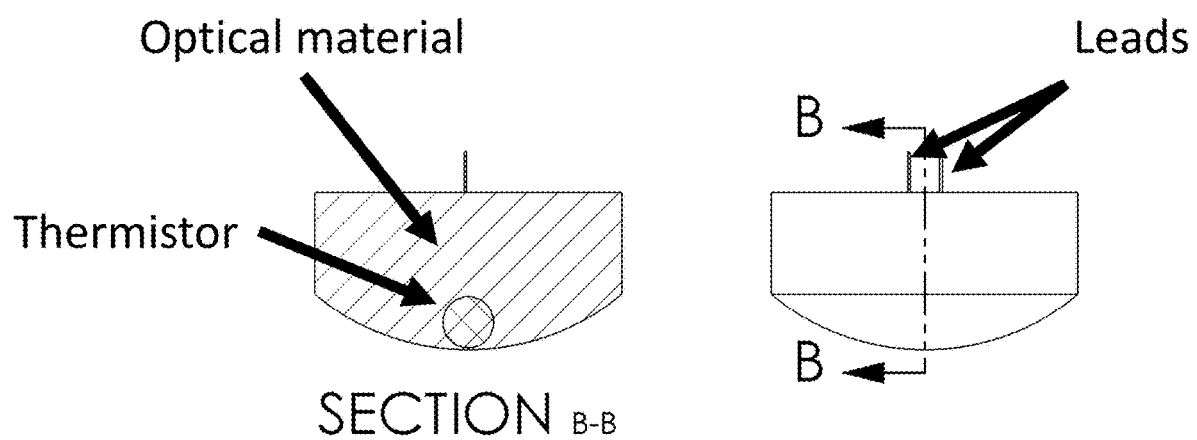
FIG. 6 shows the thermistor lens which has a thermistor embedded in the lens. Leads allow for attachment to the PCB.
Figure 7:
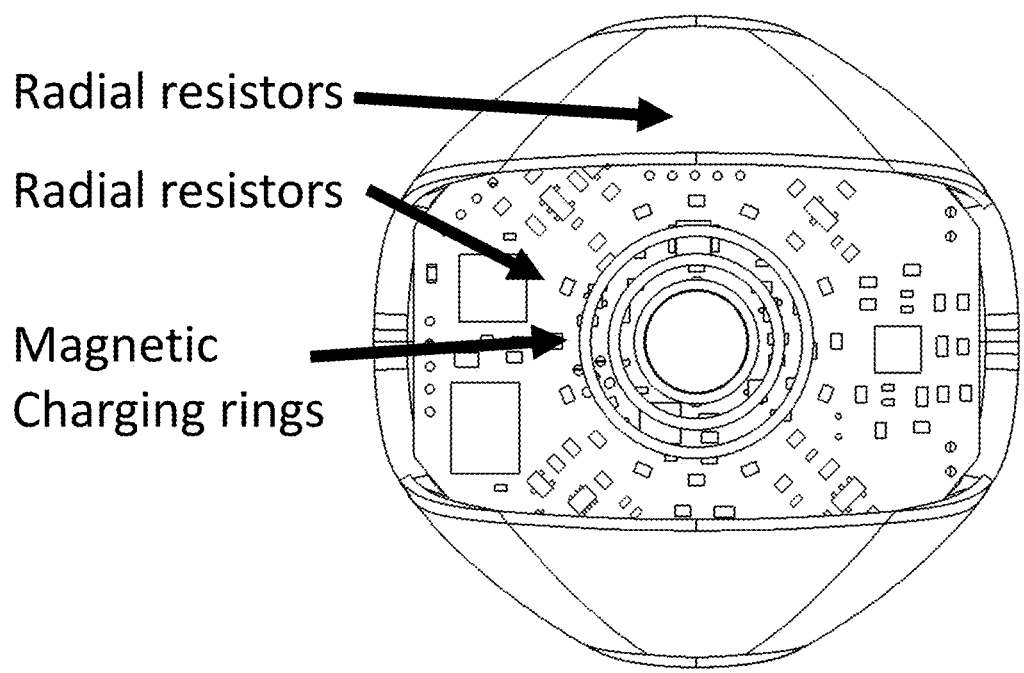
FIG. 7 shows the bottom of the vitals device without the bottom cover. The two charging rings are event. The resistors are arranged in a radial manner to allow for heating of the unit.
Figure 8:
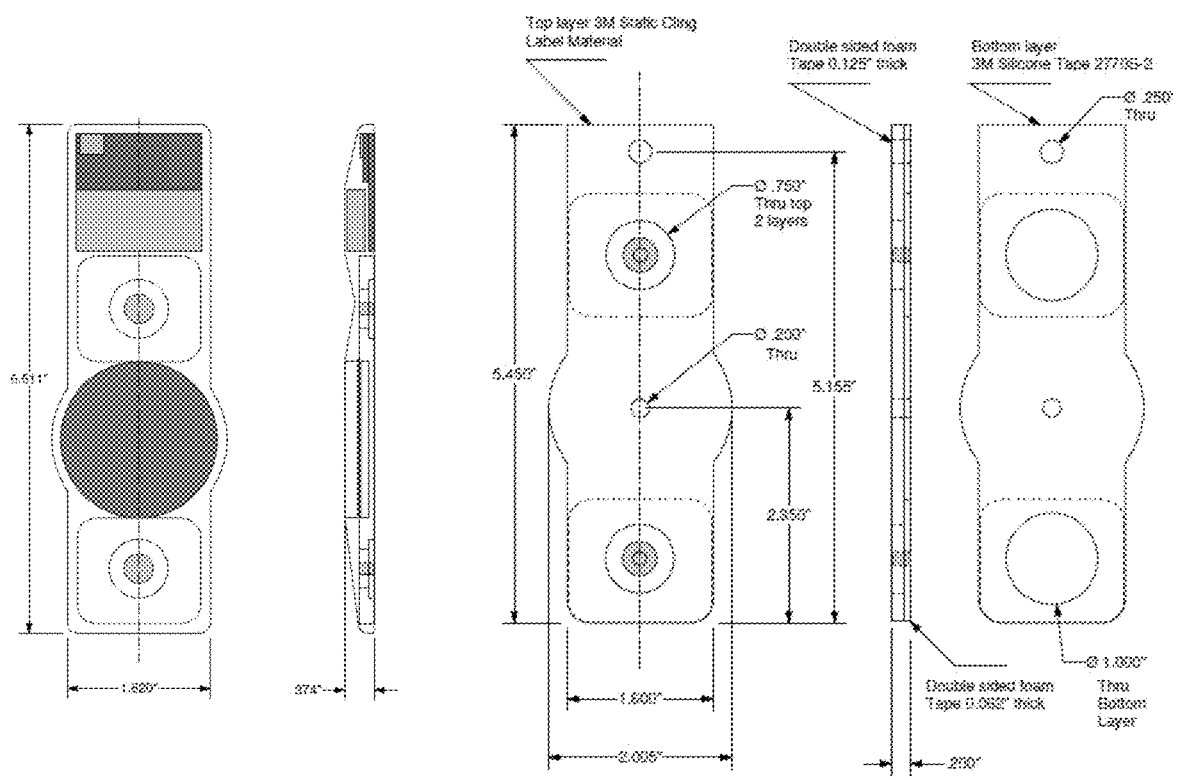
FIG. 8 shows a rectangular stack up of the vitals device. This alternate arrangement utilizes conventional electrode pads with snaps.
Figure 9:
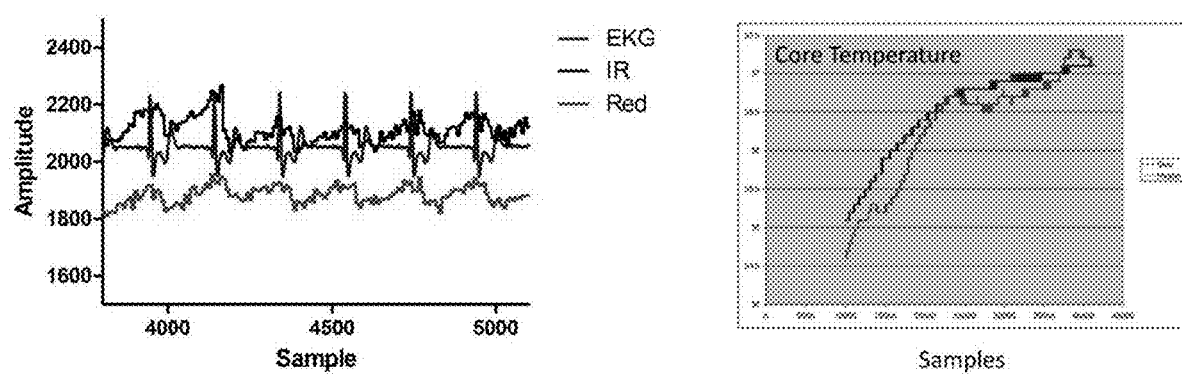
FIG. 9 shows capture of multiple data streams simultaneously off the unit, including EKG, PPG, and core body temperature.

In one embodiment, an octagonal device is utilized to carry all the sensors required for comprehensive vital signs measurements. The octagonal device measures approximately 60 mm in diameter and 10 mm in height. In order to attain this compact form factor and to be able to measure multiple vitals streams simultaneously, the sensor stack up needs to be occupying similar physical space.

In this embodiment, at the center of the PCB is the reflective pulse oximeter surrounded by a radial configuration of resistors. The resistors serve as a heating element for the system and are in the same physical plane as the reflective pulse oximeter chip and the mounts for the EKG electrodes. The method of PCB manufacture is well-known and can be done via a number of different commercial vendors. A thermistor lens is directly attached to the PCB in the center of the unit. This is done by molding clear plastic, silicone, or some other optically transparent material for the thermistor lens. The plastic can be polycarbonate, acrylic, clear urethane, or a thermoplastic elastomer. Silicone can be liquid silicone, curable silicone, or some otherwise clear silicone. The clear material contacts the PCB, encapsulates the reflective pulse oximeter chip, and the thermistor. This stack up creates a single element that emits infrared light, red light, measures temperature, and collects photoplethysmograph signals. Depending on the different material utilized, the thermistor lens can be injection molded, soft molded, or otherwise attached onto the PCB to ensure a uniform, clear material is in the central portion of the vitals unit.

There are at least two, ideally three to four, high precision (+/−0.1° C.) thermistors in the unit. The thermistors are ideally arranged in a vertical stack up configuration, with one in the thermistor lens. The clear, thermistor lens material should have a low thermal conductivity, ideally less than 0.02 W/(m·K). The insulating nature of the material minimizes heat loss and increases the flux differential between the thermistors. The device should be sealed to prevent heat loss in the system. The outer casing should be insulating and there should be no air gaps that allow heat to escape from the unit. The thermistors measure the thermal gradient from the body and allows the core body temperature to be determined with great accuracy. Through the use of the resistive heater on the PCB, more than one temperature gradient can be attained, allowing determination of the core body temperature.

The vitals pad allows for attachment of the device to the body and for continuous monitoring of multiple data streams for the vitals. The vitals pad has adhesive on both sides of it, allowing attachment to the body and the device for continuous measurement. The colors of the device side and the skin side of the vitals pad are different to allow for orientation of top and bottom for the user. At least one of the colors should be dark to prevent external light from reaching the optical sensor. This allows for The adhesiveness can be adjusted on both sides depending on the duration of use. There are two half moon gel pad regions on the unit, allowing direct contact of the skin with the electrically conductive gel pad and then to the EKG electrodes. The circular aperture in the center allows the thermistor lens to protrude through and be in contact with the skin for good optical and thermal contact. The vitals pads are designed to be single use and replaced with each data logging.

There are two EKG electrodes on the unit. These are designed electrodes and also allow for contact with the gel pad for measurement of a one-lead EKG. They are made of gold-plated brass for optimal electrical conduction. Contact with the gel pads allow for conduction of small electrical signals from the body into a recognized EKG signal consisting of a P-wave, QRS complex, and T-wave. The one-lead EKG is useful for measurement of basic electrical activity from the heart. As the heart contracts and conducts electrical signals, this is measured on the surface of the body. The ideal attachment location of the vitals device is on the chest or sternum, although other area may also give adequate signal for measurement of a one-lead EKG.

Other types of EKG pads can be possible in other embodiments, such as the strap embodiment. This utilizes two conventional, off-the-shelf EKG pads with snap hooks that allow for reversible attachment to the sensor. This alternate approach allows for use of traditional electrodes and can be helpful when ensuring compatibility with existing types of medical devices. In all cases, the EKG gel pads should position the thermistor lens so that it is touching the skin for thermal and optical measurements.

There is a power button for actuation of the device. LED indicators alert the user as to when it is on and the state of the device (on, measuring data, etc.). Other types of indicators can also be introduced into the system, including vibratory alerts since the user cannot visualize the LED indicators during continuous wearing of the device. The alerting indicators allow embedded code on the device to communicate with the user. For instance if the heart rate is above normal limits, then the device will indicate to the user the possibility of an abnormal event.

Data is transmitted from the sensor to an app using Bluetooth Low Energy (BLE). This allows for wireless data transmission using minimal battery power. The PCB has a BLE chip that is on the top side of the PCB, away from the skin. This allows it to be accessible for communications and is not blocked. The mechanical package is such that it allows enough clearance for the BLE chip to give adequate communications with the client BLE device such as a phone or tablet running an app. Onboard memory, such as flash, allows local data storage when the vitals device is not communicating to its BLE client. This allows for continuous discontinuous operation where the device can be worn and collecting data without the need for a receiving BLE client. Data can be downloaded from the onboard memory to another device.

In one embodiment, there are magnetic contacts for charging and data transfer. In one particular arrangement, the charging contacts for positive and negative are concentric circles. Placement of the vitals device onto protruding pogo pins on a receiving dock allows recognition of the vitals device and charging to occur. Three pogo pins are required: positive, negative, and sense. In this manner, if only two pins are contacted, no current will be drawn. The concentric charging rings allow for orientation independent placement of the unit onto the charging dock. The rings are made of a magnetic material such as stainless steel 430 and magnets are placed on the receiving dock. In this manner, the magnets serve to help register the charging rings onto the pogo pins for correct contact.

High speed data transfer from the vitals device to another device is required so that data stored on the device can be readily accessed. BLE has data limitations so ideally the data transfer mechanism be infrared (IR) or serial data transfer. For IR data transfer, an IR transmitter is embedded in the central thermistor lens with a receiving photodiode on the dock. This arrangement allows use of the central thermistor lens, adding to the multi-functional stack in the center of the unit. An alternate approach is to utilize metal magnetic contacts for high speed serial or parallel data transfer.

In one embodiment, the device has an octagonal shape. Other shapes may be possible including rectangular strap form, circular, triangular, or pentagonal. The part integration will be similar in these cases.

Those skilled in the art will recognize, or be able to ascertain using no more than routine experimentation and/or engineering, many equivalents to the specific embodiments of the invention described herein. The scope of the present invention is not intended to be limited to the above Description, but rather is as set forth in the claims that follow.

What is claimed is:

1. An integrated vitals sensor comprising:
    a reflective pulse oximeter;
    a plurality of thermistors, comprising at least one first thermistor and at least one second thermistor, in proximity to the reflective pulse oximeter;
    an outer casing configured to:
        house the plurality of thermistors; and
        form an air-tight seal around the plurality of thermistors and the reflective pulse oximeter; and
    a single lead EKG, wherein the integrated vitals sensor is configured to be in proximity to a wearer's skin and the at least one first thermistor is configured to be in closer proximity to the wearer's skin than the at least one second thermistor, such that the plurality of thermistors are configured to measure a heat gradient from the direction of the wearer's skin.

2. The sensor of claim 1 wherein the reflective pulse oximeter and the single lead EKG are integrated into a single circuit board.

3. The sensor of claim 1 wherein the reflective pulse oximeter, the single lead EKG, the resistive heater, and at least one of the plurality of thermistors are integrated into a single circuit board.

4. The sensor of claim 1 further comprising a wireless transceiver.

5. The sensor of claim 4 wherein the wireless transceiver uses Bluetooth Low Energy.

6. The sensor of claim 1 further comprising a double-sided adhesive gel pad to permit the sensor to be worn in contact with skin.

7. The sensor of claim 1 wherein the thermistor is embedded in a lens.

8. The sensor of claim 7 wherein the lens is positioned to be in contact with the skin when the sensor is worn in contact with the skin.

9. An integrated vitals sensor comprising:
    a reflective pulse oximeter;
    a single lead EKG;

a first thermistor, wherein the first thermistor is configured to detect core body temperature;

a second thermistor, such that the first thermistor and the second thermistor are configured to measure a heat gradient from the direction of a wearer's skin;

an outer casing, wherein the outer casing is configured to:
   house the first thermistor and the second thermistor; and
   insulate the first thermistor and second thermistor from the ambient air; and a resistive heater, wherein at least one thermistor is in communication with the resistive heater.

10. The sensor of claim 9, further comprising a double-sided adhesive gel pad to permit the sensor to be worn in contact with skin, wherein a color of a first side of the adhesive gel pad is different than a color of a second side of the adhesive gel pad.

11. The sensor of claim 9, further comprising a double-sided adhesive gel pad, wherein at least a first portion of the gel pad has a dark color that is configured to prevent external light from reaching the sensor.

12. The sensor of claim 9, further comprising at least one resistive heater, wherein the at least one resistive heater, the single lead EKG, the first thermistor, and the reflective pulse oximeter are integrated into a single circuit board.

13. The sensor of claim 9, further comprising a plurality of resistors arranged in a radial configuration around the reflective pulse oximeter.

14. The sensor of claim 9, wherein the sensor is further configured to detect at least one of heart rate, respiratory rate, EKG, and SpO2.

15. The sensor of claim 9, wherein the reflective pulse oximeter is located between the first thermistor and the second thermistor.

16. A method of manufacturing an integrated vitals sensor, the method comprising:
   providing a reflective pulse oximeter;
   providing a single lead EKG;
   providing a first thermistor;
   providing a second thermistor, such that a difference in temperature readings from the first thermistor and the second thermistor from the direction of a wearer's skin can be used to calculate core body temperature of the wearer;
   enclosing the first thermistor and the second thermistor in an outer casing;
   providing a circuit board;
   providing a resistive heater;
   connecting the reflective pulse oximeter, the single lead EKG, the resistive heater; and
   the first thermistor to the circuit board, the connection causing electrical contact between the circuit board, the reflective pulse oximeter, the single lead EKG, and the first thermistor; and
   positioning the second thermistor, such that the second thermistor is in communication with the resistive heater.

17. The method of claim 16, further comprising:
providing an infrared transmitter;
providing a central thermistor lens; and
embedding an infrared transmitter into the central thermistor lens.

18. The method of claim 16, further comprising:
providing a plurality of resistive heaters;
connecting the plurality of resistive heaters to the circuit board, such that the plurality of resistive heaters is connected radially around the reflective pulse oximeter.

* * * * *